United States Patent [19]

Harnden et al.

[11] 4,387,249

[45] Jun. 7, 1983

[54] PROCESS FOR THE MANUFACTURE OF DIETHYLENETRIAMINE

[75] Inventors: Robert M. Harnden, Russellville, Ark.; Donald W. Calvin, Lake Jackson, Tex.

[73] Assignee: The Dow Chemical Company, Midland, Mich.

[21] Appl. No.: 332,288

[22] Filed: Dec. 18, 1981

[51] Int. Cl.$^3$ ............................................. C07E 85/20
[52] U.S. Cl. .................................. 564/488; 564/511; 564/512
[58] Field of Search ................................. 564/512, 488

[56] References Cited

U.S. PATENT DOCUMENTS

| | | | |
|---|---|---|---|
| 2,436,311 | 2/1948 | Larson et al. | 260/309 |
| 2,514,830 | 7/1950 | Duschinsky et al. | 260/570.9 |
| 2,526,757 | 10/1950 | Larson et al. | 260/309.9 |
| 3,121,115 | 2/1964 | Meuly | 260/570.5 |
| 3,591,639 | 7/1971 | Tiefenthal et al. | 564/488 |
| 3,592,852 | 7/1971 | Potts et al. | 564/488 |
| 3,714,259 | 1/1973 | Lichtenwalter et al. | 260/583 P |
| 4,036,881 | 7/1977 | Brennan et al. | 260/583 P |
| 4,044,053 | 8/1977 | Brennan et al. | 260/583 P |
| 4,103,087 | 7/1978 | Brennan | 564/78 |

FOREIGN PATENT DOCUMENTS 34-28467 1/1962 Japan .................................. 564/488

*Primary Examiner*—Paul F. Shaver
*Attorney, Agent, or Firm*—A. J. Young

[57] ABSTRACT

The present invention provides a selective process for the manufacture of diethylenetriamine from ethylenediamine, ethanolamine, and urea. The process comprises a reaction cycle in which ethylenediamine, ethanolamine, and urea are first reacted in step (a) to form aminoethylethyleneurea and ethyleneurea, which in turn are hydrolyzed in a second reaction step (b) to diethylenetriamine and ethylenediamine. The ethylenediamine made in the second reaction step (b) may be recycled to the first reaction step (a).

9 Claims, No Drawings

PROCESS FOR THE MANUFACTURE OF DIETHYLENETRIAMINE

BACKGROUND OF THE INVENTION

This invention relates to the production of diethylenetriamine. More particularly, this invention relates to a cyclic two-step process for the production of diethylenetriamine from ethylene diamine, monoethanolamine and urea.

It is known that diethylenetriamine can be made by the reaction of ethylene dichloride with excess ammonia, followed by caustic hydrolysis of the amine hydrochloride salt thereby formed. A homologous mixture of ethylene amines results from this process, ranging from ethylenediamine to pentaethylenehexamine. Product selectivity is controlled mainly by varying the ethylene dichloride to ammonia ratio. A selectivity to ethylenediamine of about ninety percent can be achieved by a proper choice of this ratio, but selectivity to diethylenetriamine or higher homolog is poor. However, a method for preparing diethylenetriamine with a high degree of selectivity in high yields with little or no nonuseable by-products being formed is not known.

SUMMARY

In general, this invention provides a process for making diethylenetriamine which includes the steps of (a) reacting ethylenediamine, ethanolamine, and urea to form aminoethylethyleneurea, ethyleneurea, and ammonia; and (b) hydrolyzing the aminoethylethyleneurea and ethyleneurea formed in step (a) to diethylenetriamine and ethylenediamine. The process may further include a step (c) of recycling the ethylenediamine formed in step (b) back to step (a).

It is an object of this invention to provide a process for the manufacture of diethylenetriamine. It is a further object of this invention to provide a process which selectively yields diethylenetriamine as the major product. It is a further object of the invention to provide a process whereby diethylenetriamine can be produced in a substantially pure form without the need for additional costly separation steps. It is a further object of the invention to provide a process whereby one of the reaction products can be recycled as a reactant. Other objects of the invention will be apparent to those skilled in the art from the more detailed description which follows.

DESCRIPTION OF THE PREFERRED EMBODIMENTS

The following description illustrates the manner in which the principles of the present invention are applied, but is not to be construed as in any sense limiting the scope of the invention.

More specifically, this process comprises the steps of (a) reacting ethylenediamine, ethanolamine, and urea in an inert atmosphere to form aminoethylethyleneurea, ethyleneurea and ammonia; and (b) hydrolying the aminoethylethyleneurea and ethyleneurea formed in step (a), in an inert atmosphere and in the presence of a Brönsted base catalyst, to form diethylenetriamine and ethylenediamine.

The Brönsted base used in the hydrolysis reaction of step (b) is preferably the hydroxide of an alkali metal, and, more preferably, is an aqueous solution of sodium hydroxide. When sodium hydroxide is used to catalyze the hydrolysis reaction, sodium carbonate is formed as a by-product. The reaction of step (a) is beneficially carried out at a temperature between about 260° C. and about 320° C.; preferably between about 280° C. and about 300° C.; and most preferably between about 285° C. and about 295° C. The hydrolysis reaction of step (b) is beneficially carried out at a temperature between about 150° C. and about 250° C.; preferably between about 190° C. and about 210° C.; and most preferably between about 195° C. and about 205° C.

As herein defined the phase "inert atmosphere" means an atmosphere which is substantially nonreactive with reactants or products of the present invention. For example, a process atmosphere which excludes air, such as nitrogen, may be beneficially used to prevent undesirable oxidation and charring of the reactants or products.

For the reaction step (a), the mole ratio of ethylenediamine to urea to ethanolamine is beneficially between about 1/1/1 to about 3/1.25/1, and preferably about 3/1.25/1. For the hydrolysis step (b), the weight ratio of water to sodium hydroxide to aminoethyleneurea and ethyleneurea is beneficially between about 6/1/1 and about 12/1.5/1, and preferably about 6.4/1.1/1.

The preferred manner of carrying out reaction steps (a) and (b) is as follows. A reactor is sealed and cooled with ice, then evacuated to about ten millimeters of mercury pressure and purged with an inert gas, to remove air. This procedure is repeated five or six times. Nitrogen is the preferred inert gas, but any other inert gas such as helium may be used. The present invention will now be further illustrated by means of the following examples, which are illustrative only and are not intended to limit in any sense the scope of the invention.

EXAMPLE 1

A one-liter pressure vessel (Parr-bomb reactor) was charged with 96.0 grams (1.6 moles) of ethylenediamine, 34.5 grams (0.53 moles) of ethanolamine, and 39.5 grams (0.66 moles) of urea. The reactor was sealed and placed in an ice bath, then evacuated to about ten millimeters of mercury pressure and purged with nitrogen. This procedure was repeated five times, for a total of six evacuations and nitrogen purges. The reactor was then placed in a heating jacket and heated to 280° C., with continuous stirring, for a total time of two hours. The reactor was then cooled to ambient temperature and vented down to atmospheric pressure. Analysis of the reaction-product mixture showed a ninety-three percent conversion of the ethanolamine, with 81.9 percent selectivity to aminoethylethyleneurea and 14.5 percent selectivity to ethyleneurea.

EXAMPLE 2

A thirty-five gram aliquant of the reaction-product mixture from the reaction in Example 1 above was placed in a second one-liter pressure vessel. Forty grams (one mole) of sodium hydroxide pellets and two-hundred grams (11.1 moles) of water were added to the second pressure vessel. The vessel was sealed, then placed in an ice bath and evacuated and purged with nitrogen as described in Example 1, above. The vessel was then heated for one hour with stirring at a temperature of 200° C. The vessel was cooled to ambient temperature and vented to atmospheric pressure. Analysis of this reaction-product mixture showed a quantitative conversion of the aminoethylethyleneurea and ethyleneurea to diethylenetriamine and ethylenediamine, respectively. Thus, the overall conversion of the original ethanolamine was ninety-three percent, with an overall selectivity of 81.9 percent to diethylenetriamine and 14.5 percent to ethylenediamine.

EXAMPLE 3

The two-step synthesis exemplified by Examples 1 and 2, above, was repeated. The only difference in the experimental conditions was a reaction time of four hours at 285° C. in the first-step reaction (Example 1). The conversion of the original ethanolamine was quantitative, with 81.3 percent selectivity to diethylenetriamine and 13.8 percent selectivity to ethylenediamine.

EXAMPLES 4 THROUGH 9

The hydrolysis step was carried out in the same manner as in Examples 1, 2, and 3, above. The first reaction step (Example 1) between ethylenediamine, ethanolamine, and urea was carried out in a continuous flow system. The flow system comprised a reagent cylinder, two knockout pots, an ammonia scrubber containing four-percent boric acid, a sandbath for temperature control, a pump for inducing and maintaining flow of reactants and products, and valves for the knockout pots. This apparatus was operated in the following manner: a solution of ethylenediamine, urea, and ethanolamine in a mole ratio of 3/1.25/1, respectively, was heated and then pumped from the nitrogen-padded reagent cylinder by a Milton Roy positive-displacement pump through a stainless-steel coiled reactor heated by the fluidized sandbath. A back pressure of between about five hundred and about fifteen hundred pounds per square inch gauge was maintained in the reaction system by a control valve. Non-condensable components of the reaction-product stream were collected in the knockout pots, and the ammonia evolved by the reaction was absorbed by the solution of four-percent aqueous boric acid in the scrubber.

The experimental conditions and results are shown in the following Table 1. In the tabulation, "temperature" and "time" designate reaction temperature and residence time through the stainless-steel coiled reactor for the first reaction, step (a).

TABLE 1

| Example No. | Temperature (°C.) | Time (Hours) | (1) Conversion (Percent) | Selectivity (Percent) | | |
|---|---|---|---|---|---|---|
| | | | | (2) EDA | (3) DETA | Byproducts |
| 4 | 295 | 3.0 | 75 | 24.7 | 74.6 | 0.7 |
| 5 | 295 | 3.7 | 94 | 11.3 | 81.0 | 7.7 |
| 6 | 285 | 3.7 | 82 | 21.8 | 73.5 | 4.7 |
| 7 | 305 | 3.7 | 100 | 17.3 | 62.8 | 19.9 |
| 8 | 295 | 4.4 | 98 | 11.4 | 69.9 | 18.7 |
| 9 | 305 | 3.0 | 94 | 15.4 | 68.6 | 16.0 |

(1) Percent conversion of the original ethanolamine reactant.
(2) EDA means ethylenediamine.
(3) DETA means diethylenetriamine.

While certain representative embodiments and details have been shown for the purpose of illustrating the present invention, it will be apparent to those skilled in the art that various changes and modifications can be made therein without departing from the spirit and scope of the invention.

What is claimed is:

1. A process for the manufacture of diethylenetriamine, comprising the steps of:
   (a) reacting ethylenediamine, ethanolamine, and urea to form aminoethylethyleneurea, ethyleneurea, and ammonia; and
   (b) hydrolyzing the aminoethylethyleneurea and ethyleneurea formed in step (a) to diethylenetriamine and ethylenediamine, respectively.

2. The process of claim 1, which further comprises the step of:
   (c) separating and recycling the ethylenediamine formed in step (b) back to step (a).

3. The process of claim 1 or 2, wherein reaction steps (a) and (b) are carried out in an atmosphere of inert gas.

4. The process of claim 3, wherein the hydrolysis step (b) is carried out in the presence of a Brönsted base catalyst.

5. The process of claim 4, wherein the base is a hydroxide of an alkali metal.

6. The process of claim 5, wherein the base is an aqueous solution of sodium hydroxide.

7. The process of claim 1 or 2, wherein the hydrolysis step (b) is carried out in the presence of a Brönsted base catalyst.

8. The process of claim 7, wherein the base is a hydroxide of an alkali metal.

9. The process of claim 8, wherein the base is an aqueous solution of sodium hydroxide.

* * * * *